(12) United States Patent
Walck

(10) Patent No.: US 8,439,216 B1
(45) Date of Patent: *May 14, 2013

(54) TELESCOPIC SPECIMEN HOLDER

(75) Inventor: Scott D Walck, Oceanside, CA (US)

(73) Assignee: South Bay Technology, Inc., San Clemente, CA (US)

( * ) Notice: Subject to any disclaimer, the term of this patent is extended or adjusted under 35 U.S.C. 154(b) by 194 days.

This patent is subject to a terminal disclaimer.

(21) Appl. No.: 12/694,003

(22) Filed: Jan. 26, 2010

Related U.S. Application Data

(63) Continuation of application No. 11/495,294, filed on Jul. 28, 2006, now Pat. No. 7,723,701.

(60) Provisional application No. 60/703,727, filed on Jul. 29, 2005.

(51) Int. Cl.
*B65D 6/00* (2006.01)
*B65D 8/14* (2006.01)

(52) U.S. Cl.
USPC ............... 220/8; 141/65; 141/66; 250/430

(58) Field of Classification Search ............ 250/440.11, 250/442.11, 310, 311, 428, 522.1, 507.1; 220/8, 592.27; 206/524.8; 141/65, 66; 222/386
See application file for complete search history.

(56) References Cited

U.S. PATENT DOCUMENTS

| | | | |
|---|---|---|---|
| 3,211,368 A | * | 10/1965 | Sbanely ........................ 494/2 |
| 3,937,847 A | | 2/1976 | Elkins et al. |
| 4,052,320 A | * | 10/1977 | Jakubowicz ................. 210/516 |
| 4,260,082 A | | 4/1981 | Rooney et al. |
| 4,475,711 A | * | 10/1984 | Rountry ........................ 251/85 |

(Continued)

OTHER PUBLICATIONS

Information specific to liquid nitrogen, http://www.safety.seas.harvard.edu/services/nitrogen.html, (C) President and Fellows of Harvard College, available online since Jul. 31, 2003, accessed May 20, 2009.

*Primary Examiner* — David A Vanore
*Assistant Examiner* — Brooke Purinton
(74) *Attorney, Agent, or Firm* — Stout, Uxa, Buyan & Mullins, LLP; Donald E. Stout

(57) ABSTRACT

A two-part container for preserving material samples during storage and transport is separable and can be sealed with the presence of an elastomeric O-ring and internal threads on each part of the container. In the configuration at which the threads first engage between the two halves of the container, there is a small hole in the outer top part just above the O-ring of the bottom mating part. When the two container parts are mated and the sealing O-ring is below the small hole, inert gas can be made to flow through an inlet valve, into the container, and out through the small hole. In this configuration, the inert gas flows through the container and purges the atmospheric gas, replacing it with inert gas. After a period of time, the two container parts are rotated so that the sealing O-ring moves above the small hole. This will stop the flow into and out of the container. After this, the gas inlet valve is closed to seal the inert gas in the container. After the valve is closed, the pressure in the container is increased by screwing the two parts of the container in relation to each other such that the volume of the container is decreased. Prior to opening, the efficacy of the container can be checked by releasing the gas while the container is in the compressed state.

9 Claims, 10 Drawing Sheets

U.S. PATENT DOCUMENTS

| | | | |
|---|---|---|---|
| 4,551,080 A * | 11/1985 | Geiger | 418/28 |
| 4,569,596 A * | 2/1986 | Romanchik et al. | 366/107 |
| 4,672,797 A | 6/1987 | Hagler | |
| 5,217,053 A | 6/1993 | Foster et al. | |
| 5,390,785 A | 2/1995 | Garric et al. | |
| 5,491,345 A | 2/1996 | Stoutenburgh | |
| 5,586,585 A | 12/1996 | Bonora et al. | |
| 6,629,402 B1 | 10/2003 | Zawalick | |
| 6,767,277 B2 | 7/2004 | Henry et al. | |
| 6,883,686 B2 | 4/2005 | Langlois et al. | |
| 6,966,348 B2 | 11/2005 | Steidl et al. | |
| 2006/0011868 A1 | 1/2006 | Kidron et al. | |
| 2006/0233709 A1* | 10/2006 | Goldsmith et al. | 424/9.2 |

* cited by examiner

TELESCOPIC SPECIMEN HOLDER

This application is a continuation application of the commonly assigned U.S. application Ser. No. 11/495,294, filed Jul. 28, 2006, now U.S. Pat. No. 7,723,701 and now allowed, which in turn claims the benefit under 35 U.S.C. 119(e) of the filing date of Provisional U.S. Application Ser. No. 60/703,727, entitled Specimen Preservation System, and filed on Jul. 29, 2005. Each of the above referenced applications are expressly incorporated herein by reference, in their entirety.

BACKGROUND OF THE INVENTION

This invention relates to a specialized container that allows a process or method of replacing the atmospheric air that is in a container, which is composed of reactive gas species such as oxygen and water vapor, with an inert gas species such as nitrogen, carbon dioxide, argon, and the like, so that a material or the surface of the material disposed in the container does not undergo reactions such as oxidation during storage and/or transportation. Typically, the inventive container is used for the preservation of microscopy or material samples that may undergo changes during the delay between the time the sample is prepared and the time when analysis of the sample occurs, wherein the change in the sample would otherwise adversely affect the results of the analysis. It also includes the preservation of ingredient materials during delays between processing steps in the synthesis of new materials.

There are many examples in microscopy, which include optical microscopy, scanning electron microscopy (SEM), transmission electron microscopy (TEM), and scanned probe microscopies (SPM), where the sample may change from its desired state because it is exposed to the reactive gas species in the atmosphere. For example, in optical microscopy, oxidation or reaction with sulfur in the air can lead to color changes seen on the sample that affect the quality and the interpretation of the image. SEM, TEM, and SPM techniques are surface sensitive and oxidation of the surface can lead to charging effects and/or the inability to examine the sample. The presence of a modified surface can lead to erroneous interpretation of the images or data acquired from samples that undergo changes. In fact, in some cases such as in electron beam back scattered diffraction (EBSD), the diffraction signal is so sensitive to the condition of the surface, that the changed surface could render the technique useless for the analysis.

There are a number of ways in which materials scientists preserve samples from the adverse effects of exposure of the samples to atmosphere. Moisture in air can be the major problem and an effective desiccant in an enclosed container will often prevent problems. Encapsulation in tubes that have been evacuated, backfilled with an inert gas, and then sealed have been effective. Exclusion of air by the use of a vacuum container will also solve the problem, providing that the vacuum generation process is sufficiently clean from oil and water vapor. To be effective, whatever method is used for the preservation of the samples requires that the concentration of the reactive gas species in the container holding the samples be decreased to very small values and maintained.

The major problem with these techniques is that they are not portable with respect to transporting samples and then resealing them after the sample has been examined at a remote site, unless identical apparatus are located at the two sites. For microscopy applications, samples are often moved between laboratories separated by great distances, and the available facilities and instrumentation will be different between the two locations. For example, when samples are moved to the laboratory where the analysis is to be made, a suitable vacuum pump or a supply of suitable high purity inert gas may not be readily available to re-seal the sample.

Another problem is presented when samples are stored for long periods or transported to another location. It is important to know whether the transport container has maintained its integrity and the samples have not been compromised prior to submitting them for rather costly analyses, but similar facilities for re-sealing the sample are often not available at the second location.

SUMMARY OF THE INVENTION

The present invention addresses the problems noted above, in part by utilizing liquid nitrogen, which is common to all electron microscopy facilities for cooling X-ray energy dispersive spectrometers, liquid nitrogen vacuum traps, and anti-contamination devices. The boil-off from liquid nitrogen is extremely pure and is relatively easy to produce. Liquid nitrogen is also readily available commercially through local suppliers. Although for the invention described below, it is assumed that liquid nitrogen is available, other sources of inert gas can also be used for the invention to work. The present invention provides a method or process for preserving a material sample during storage using an inert gas that replaces the air or other oxygen-containing gas from the volume space of a container. The use of the container also includes the preservation of ingredient materials during delays between processing steps in the synthesis of new materials. By replacing the atmospheric gas with a specific gas or gas mixture, the container may be used to provide a reactive gas under controlled conditions or to protect a reaction, such as a polymerization reaction, under a protective inert atmosphere.

The invention comprises a two-part container that separates and can be sealed with the presence of an elastomeric O-ring and internal threads on the two parts of the container. In the configuration at which the threads first engage between the two halves of the container, there is a small hole in the outer top cylinder just above the O-ring of the bottom mating cylinder. At the non-open end of either the top or bottom cylinder, a gas inlet valve is positioned. When the two parts are mated and the sealing O-ring is below the small hole, inert gas can be made to flow through the inlet valve, into the container, and out through the small hole. In this configuration, the inert gas flows through the container and purges the atmospheric gas replacing it with inert gas. The small hole ensures that the flow of the inert gas helps drag the original air out of the container. The flow can be regulated to be high initially in order to help purge the volume faster and then slowed to a small flow. After a period of time, the inert gas flowing through the container will be at or nearly at its supply purity and not contaminated with remnant gas species from the original atmosphere.

At this time, the two parts are rotated so that the sealing O-ring moves above the small hole. This will stop the flow into and out of the container. Thus, the assembly of the bottom and top parts of the container with the hole and the O-ring form the basis of an exhaust valve. After this, the gas inlet valve is closed to seal the inert gas in the container. At this point, the pressure in the cylinder is just slightly above atmospheric pressure because of the low delivery pressure during the purging stage. After the valve is closed, the pressure in the container is increased by screwing the two parts of the container in relation to each other such that the volume of the container is decreased. The increased pressure in the container does two things. First, it prevents ingress of undesirable reactive gas species into the container, and second, it gives positive proof that the samples have been protected during storage and transportation. The latter advantage is accomplished by simply opening the inlet valve while the storage container is compressed, prior to opening it. The audible sound or "whoosh" of gas out of the container, through the gas inlet valve, due to the compressed gas escaping is indicative that the container has not leaked during the storage period.

If a gaseous supply of an inert gas, such as from a nitrogen or argon cylinder or boil-off from a self-pressurized liquid nitrogen storage tank, is not available, there are two methods for delivering clean, dry nitrogen from a container of liquid nitrogen. In the first method, a plate with a hole and an elastomeric sealing surface is placed over an open, foam-insulated container or Dewar flask of liquid nitrogen and sealed. Through the hole, a diaphragm pump is used to suck dry nitrogen from the head space of the container and deliver it to the exhaust side of the diaphragm pump, where it is delivered to the inventive container through a flexible length of tubing attached between the pump and the container. This will produce a constant, low-pressure flow of nitrogen. In this configuration, dry ice can also be used as a substitute for the liquid nitrogen if the sample does not react with the CO, produced.

In the second method, an inverted funnel or tube is placed in an open-to-air foam-insulated container of liquid nitrogen. Flexible tubing is connected between the funnel and the invention. A resistive heater is placed in the large part of the inverted funnel and below the level of the liquid nitrogen. When a current flows through the heater, the liquid nitrogen boils off and is supplied to the tube. The nitrogen flow can be controlled by the amount of current supplied to the heater.

More particularly, in one aspect of the invention, there is provided a system for preserving material samples, which comprises a container having an interior volume. The container comprises a bottom portion and a top portion, wherein the bottom portion is receivable within the top portion in telescoping fashion, and the bottom portion is movable within the top portion to vary the size of the interior volume. An inlet opening is capable of being selectively opened and closed, and is adapted for connection to a source of clean inert gas, preferably nitrogen. The container further comprises an outlet opening, preferably disposed on the container top portion, which is capable of being selectively opened and closed, wherein the outlet opening is adapted for exhausting fluid from the interior volume.

A sealing O-ring is disposed on an outer surface of the container bottom portion. When the outlet opening is open, the bottom portion is disposed within the top portion such that the sealing O-ring is located just below the outlet opening, and when the outlet opening is closed, the bottom portion is disposed within the top portion, such that the sealing O-ring is located just above the outlet opening. In a preferred embodiment, the inlet opening comprises an inlet gas valve.

The inventive container is adapted for many different uses. In one application, a TEM sample holder is disposed within the interior volume for holding a TEM sample. In another application, a SEM specimen holder is disposed within the interior volume for holding a SEM specimen. The container is designed such that threads are disposed on each of the top container portion and the bottom container portion for engaging the top container portion with the bottom container portion and permitting relative movement between the top and bottom container portions. This relative movement between the bottom and top container portions cause the outlet opening to be selectively opened or closed.

If a ready source of inert gas is not available, a source of inert gas for the system can be provided, which comprises a container having liquid inert gas therein and a space above the liquid inert gas which contains vaporized inert gas. A cover is disposed over an open end of the container, and a pump is disposed on the cover. A pump inlet extends through the cover and the pump additionally has an outlet. The pump outlet is fluidly connected with the inlet opening.

An alternative source of inert gas for the inventive system may comprise a container having liquid inert gas therein and an inverted funnel disposed in the container. A wide mouth of the funnel is disposed within the liquid inert gas, and a narrow spout of the funnel is disposed above the liquid inert gas. A resistive heater is disposed within the mouth of the funnel for heating and boiling off gaseous nitrogen from the liquid nitrogen within the funnel, wherein the funnel spout is fluidly connected to the inlet opening.

In another aspect of the invention, there is provided a system for preserving material samples, which comprises a container having an interior volume, wherein the container comprises a bottom portion and a top portion. The container top portion and the container bottom portion are movable relative to one another to vary a size of the interior volume. An inlet opening is capable of being selectively opened and closed, and is adapted for connection to a source of clean inert gas. The container further comprises an outlet opening which is capable of being selectively opened and closed. The outlet opening is adapted for exhausting fluid from the interior volume, and may be opened or closed by relative movement of the top and bottom container portions.

In yet another aspect of the invention, there is disclosed a method of preserving material samples using a container having a bottom portion and a top portion, wherein the container defines an interior volume and has an inlet opening and an outlet opening. The inventive method comprises steps of introducing clean inert gas into the interior volume through the inlet opening, closing the outlet opening, closing the inlet opening, and reducing the interior volume to thereby pressurize inert gas within the interior volume to a higher pressure level. In some operating regimes, there is a substantial delay between the inert gas introducing step and the outlet opening closing step in order to permit the inert gas to fully purge the interior volume of impurities and air. In other operating regimes, wherein purging is unnecessary, the outlet opening closing step occurs prior to or simultaneously with the inert gas introducing step.

The inventive method further includes a step of assembling the container by inserting the bottom container portion telescopically into an open bottom end of the top container portion, such that the top and bottom container portions are at a first selected orientation relative to one another, such that a sealing O-ring on the bottom portion is disposed below the outlet opening which is disposed in the top portion. The assembling step occurs prior to the inert gas introducing step. The step of closing the outlet opening is preferably performed by moving the bottom portion upwardly, relative to the top portion, from the first selected orientation to a second selected orientation, wherein the sealing O-ring is disposed above the outlet opening.

The bottom container portion is telescopically received within an open bottom end of the top container portion to define the interior volume, according to the disclosed method. The interior volume reducing step is performed by moving the bottom container portion upwardly relative to the top container portion. A further step of ascertaining whether the container interior volume has maintained a pressure level substantially above exterior pressure levels by opening the inlet opening and determining whether gas is released at pressure from the interior volume may also be performed.

The invention, together with additional features and advantages thereof, may be best understood by reference to the following description taken in conjunction with the accompanying illustrative drawings. In these accompanying drawings, like reference numerals designate like parts throughout the figures.

DETAILED DESCRIPTION OF THE INVENTION

Figure 1:
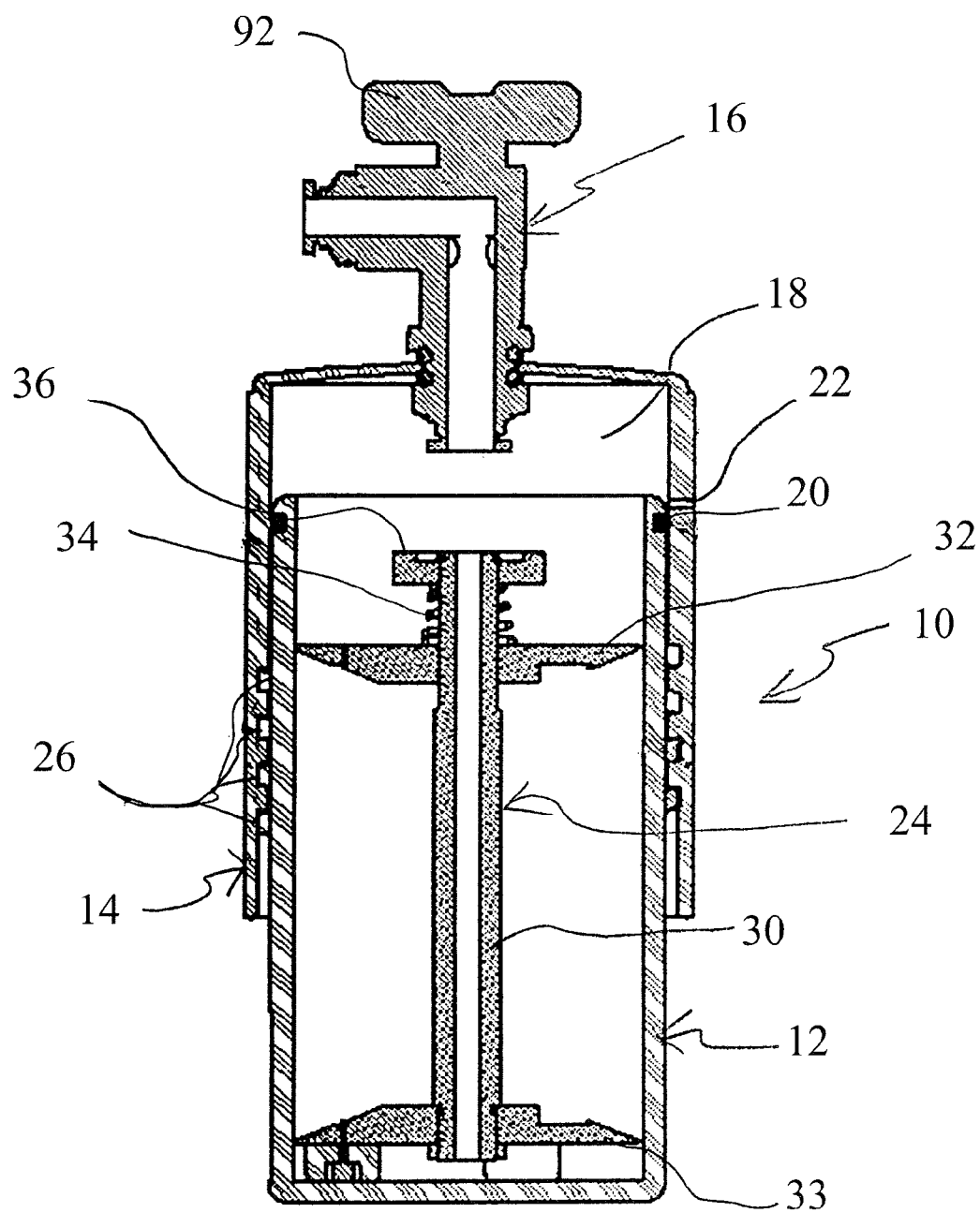
FIG. 1 shows a cross-sectional view of a container constructed in accordance with the principles of the present invention, wherein a bottom portion of the container is joined with a top portion of the container in a position wherein a sealing O-ring on the bottom portion is located below an exhaust hole on the top portion.
Figure 2:
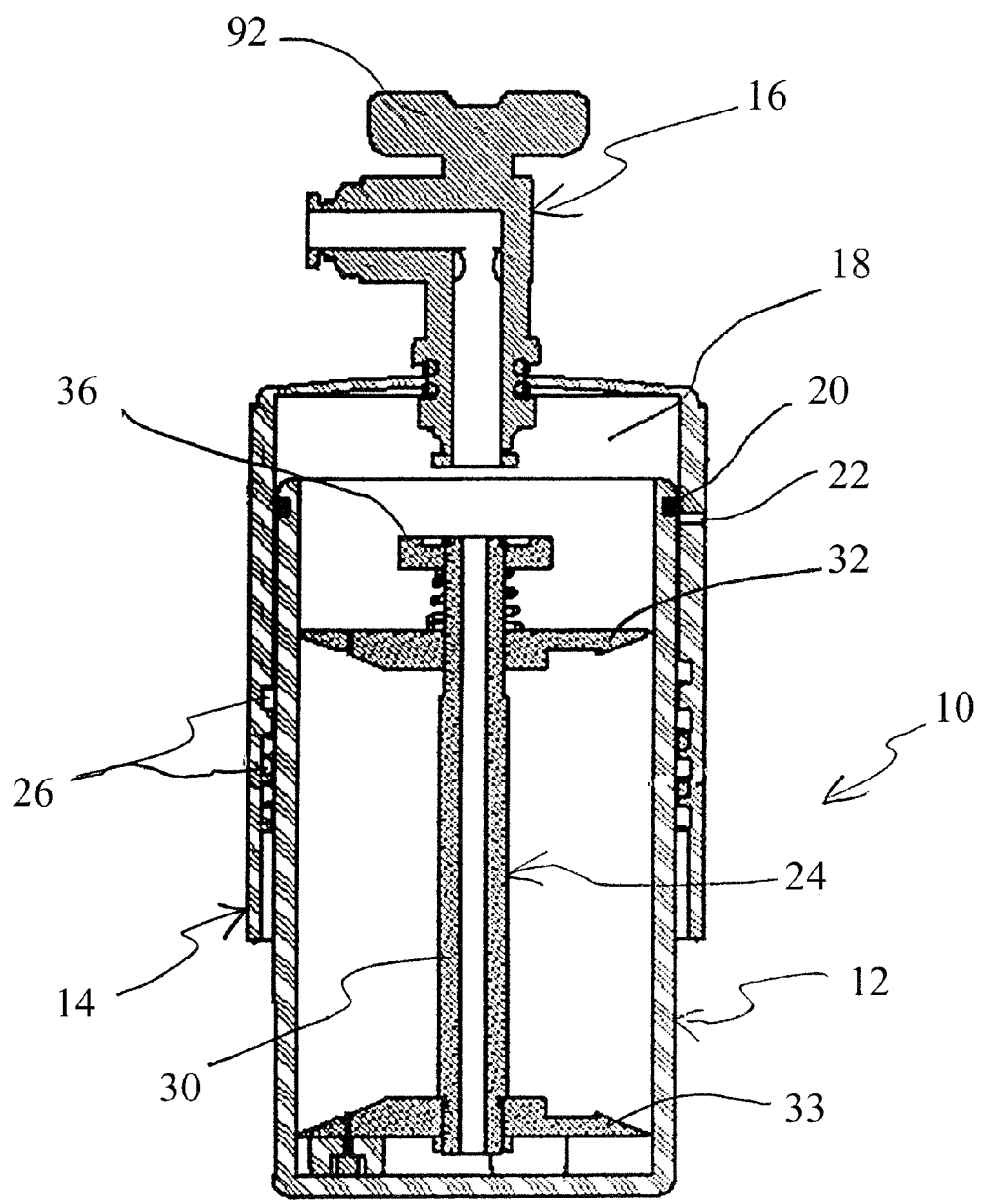
FIG. 2 is a cross-sectional view similar to FIG. 1, wherein the sealing O-ring is positioned above the exhaust hole.
Figure 3:
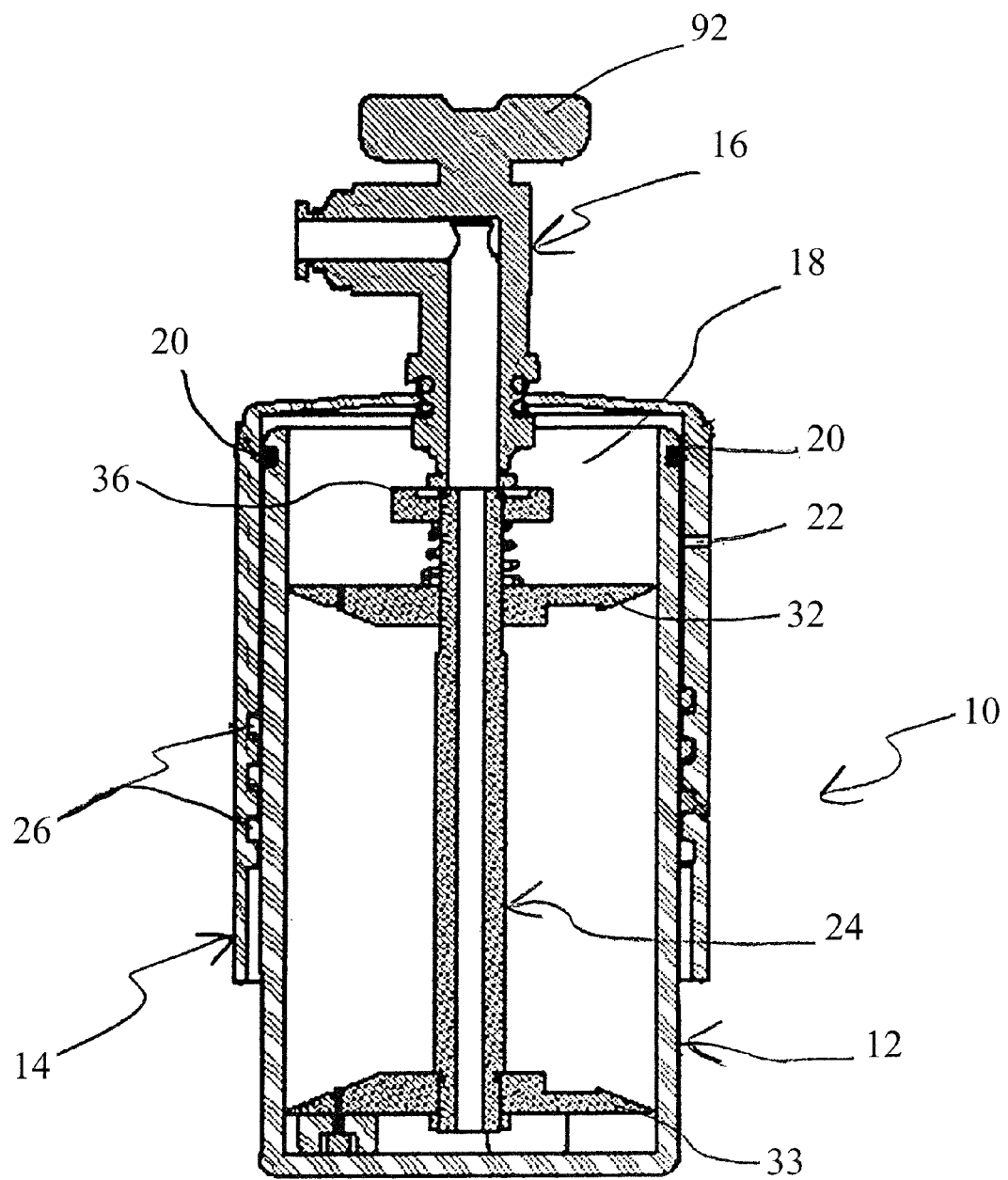
FIG. 3 is a cross-sectional view similar to FIGS. 1 and 2, wherein the two halves of the container have been fully assembled together.

Referring now more particularly to FIGS. 1-3, there is shown a container 10 which is constructed in accordance with the principles of the present invention. The container 10 comprises a bottom portion 12 and a top portion 14, which are assembled together, as shown in FIG. 1, for example, wherein the bottom portion 12 is telescopically received within the top portion 14. An inlet gas valve 16 provides fluid access to an interior chamber 18 defined by the top portion 14 of the container 10. The valve 16 may be disposed at the non-open end of either the top or bottom cylinder or container portion 14, 12, respectively, though it is preferably located at the top end of the top container portion 14, as shown. A sealing O-ring 20 is disposed between the sidewalls of the top portion 14 and the bottom portion 12 of the container 10. An outlet opening or exhaust aperture 22 is disposed in the sidewall of the top portion 14, as shown in the drawings.

A sample holder insert 24 is provided within the bottom container portion 12, as shown, which will be described in more detail hereinbelow.

Preferably, the top and bottom portions 14 and 12, respectively, of the container 10 are connected to one another by means of threads 26 on each of the two container portions, which may be engaged or disengaged by rotating one of the container portions 12, 14 relative to the other one, in conventional fashion for threaded connection methods.

Figure 4:
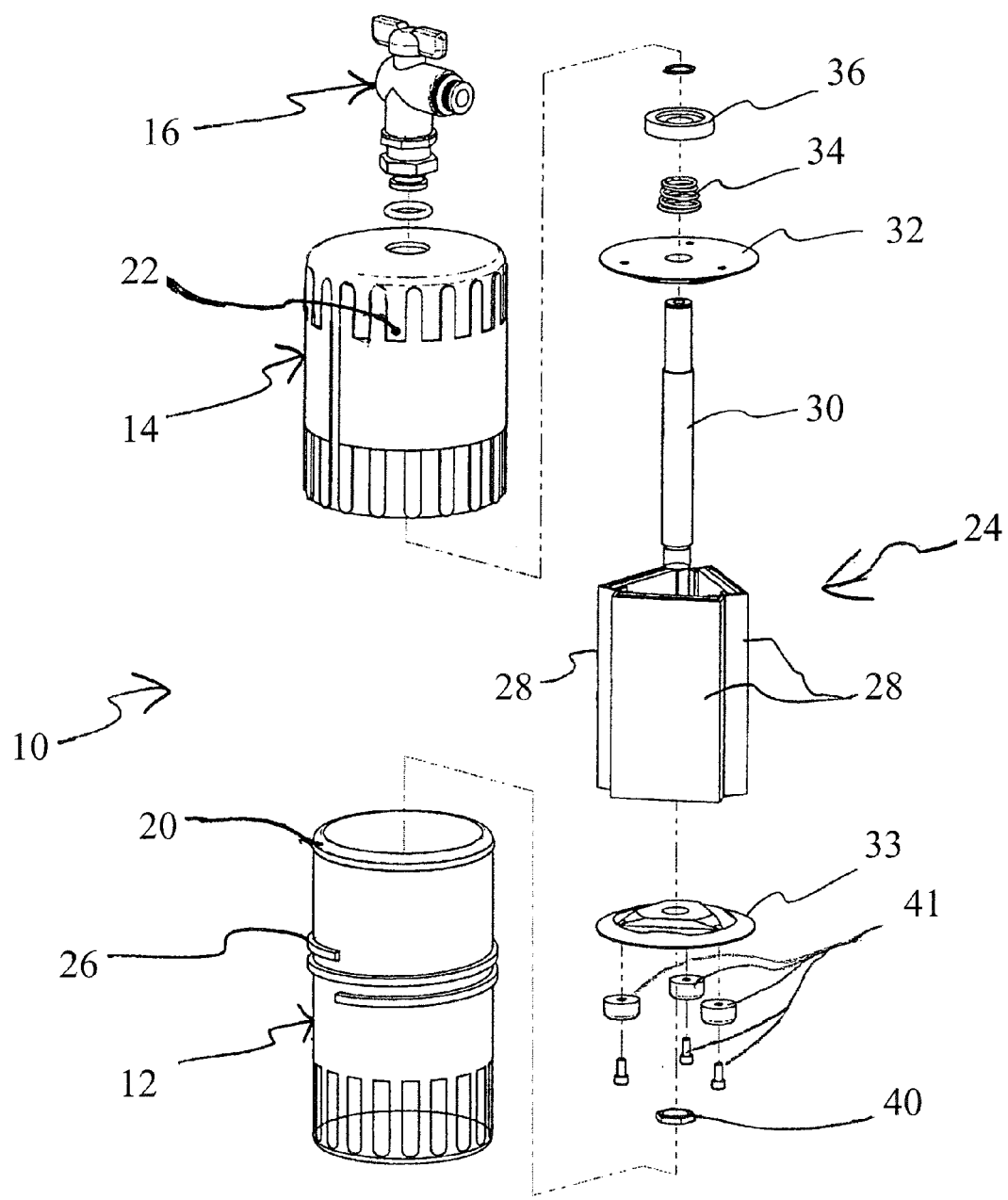
FIG. 4 is an exploded view of the container of FIGS. 1-3 showing details of a holder that is capable of holding three specially vented transmission electron microscopy grid boxes for TEM specimens.
Figure 4A:
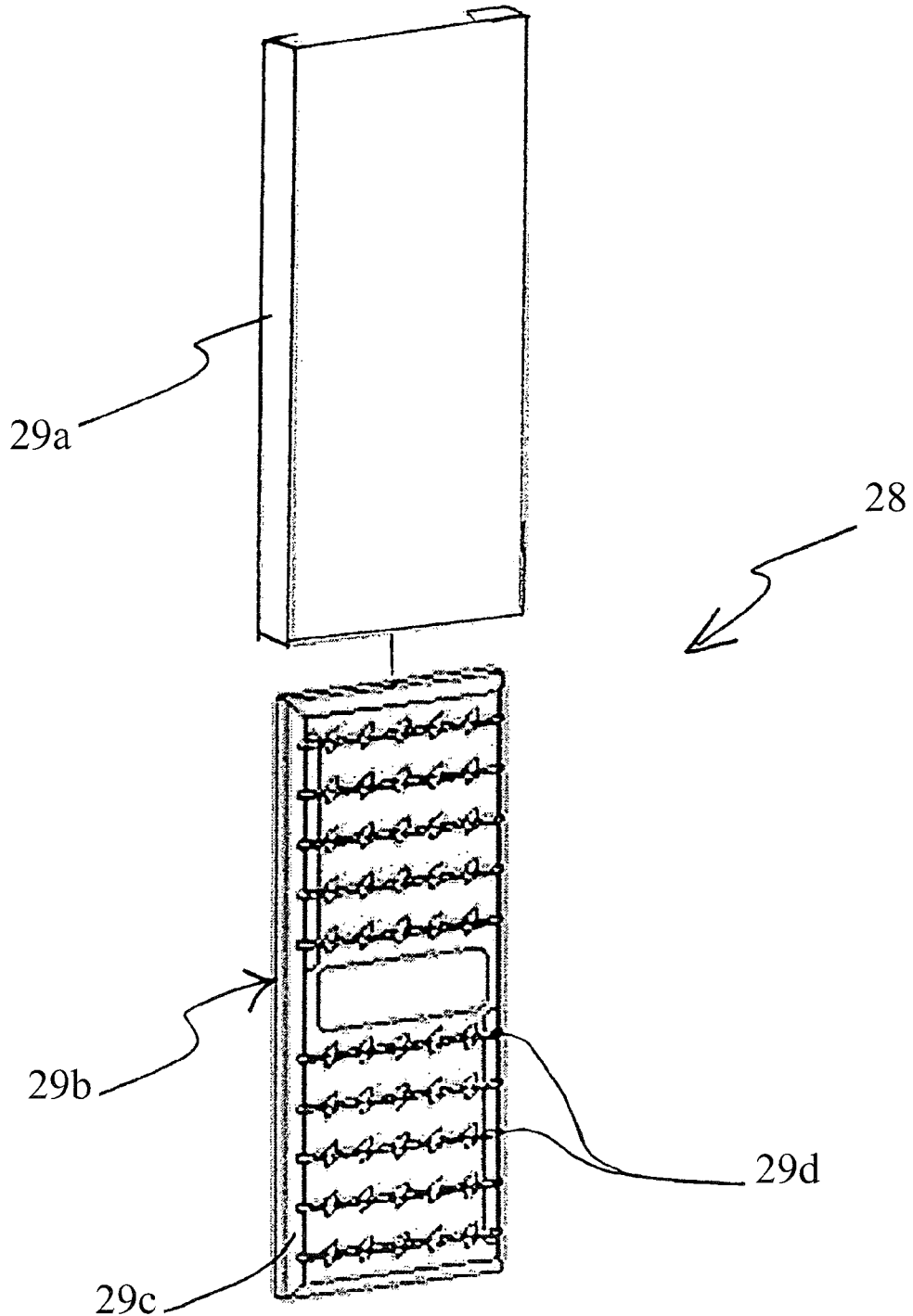
FIG. 4A is a perspective exploded view illustrating in detail the construction of one of the TEM specimen grid boxes.

FIG. 4 is an exploded view of the container 10 shown in FIGS. 1-3. As can be seen from the figure, the sample holder insert 24 may be comprised to hold three TEM grid boxes 28 arranged triangularly. The three TEM grid boxes 28 are specially vented to allow free flow of gas in order to eliminate trapped atmospheric gas and to effect a complete exchange of the atmospheric gas with the purge gas. One of the TEM grid boxes 28 is shown in greater detail in FIG. 4A. Each TEM grid box 28 comprises a clear sliding cover 29a disposable over a vented TEM retaining container 29b in which the sample is retained. A beveled edge 29c and cross cut channels 29d are provided for gas passage.

A support post 30 extends through a top clamping plate 32 and a bottom clamping plate 33. A spring 34 is supported on the post 30, and a retainer cap 36 is disposed above the spring 34, and functions as a handle. The spring 34 compresses the top clamping plate 32 against the three TEM grid boxes 28 and keeps them secured against the bottom plate 33, which is secured in place using fastener hardware 40. A plurality of leg assemblies 41 are attached to the bottom clamping plate 33.

Figure 5:
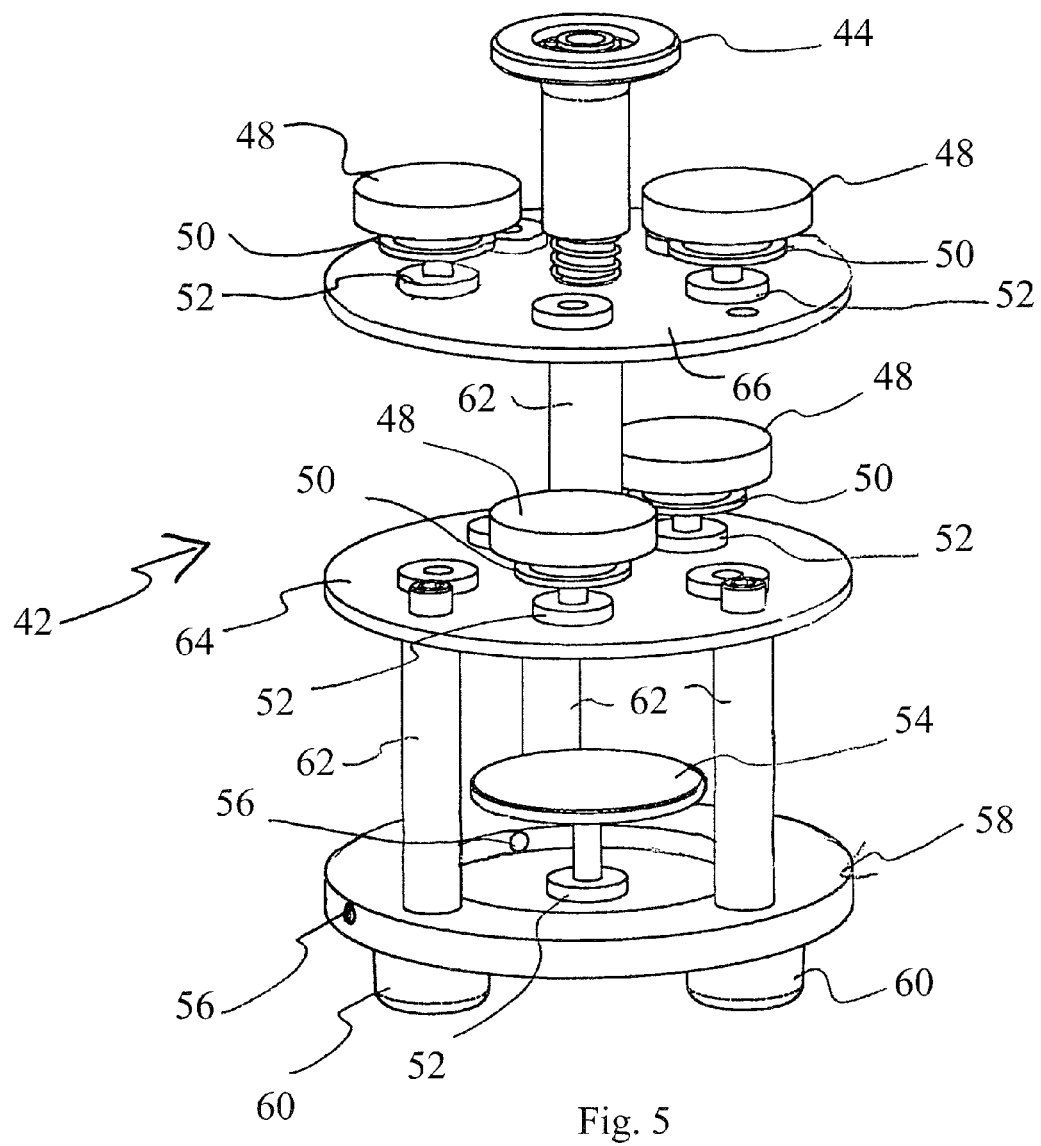
FIG. 5 is a perspective view illustrating a sample holder for SEM specimens mounted on ⅛" pin stubs, usable in conjunction with the container shown in FIGS. 1-3.
Figure 6:
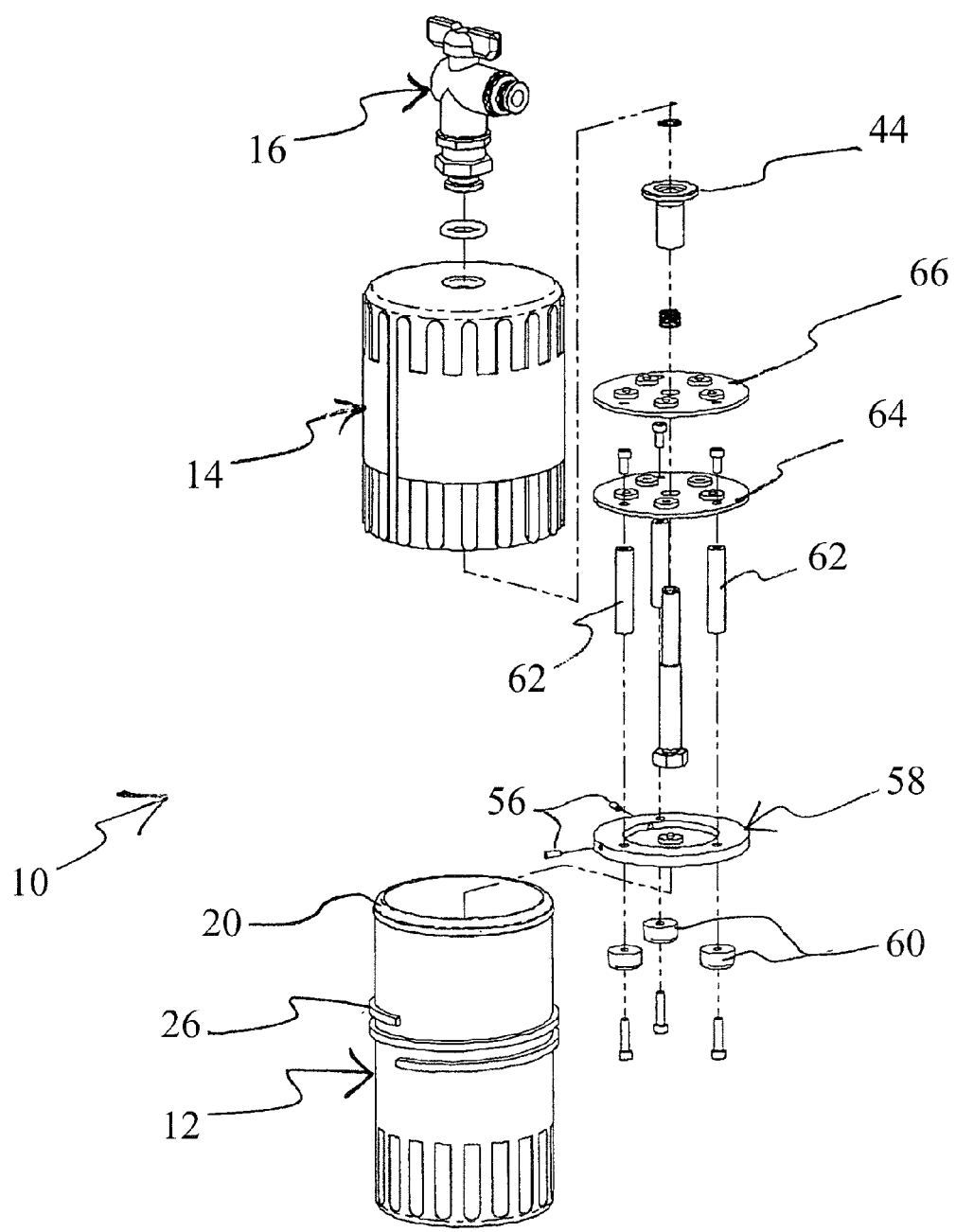
FIG. 6 is an exploded view similar to FIG. 4, illustrating the sample holder of FIG. 5 assembled within the container of FIGS. 1-3.
Figure 7:
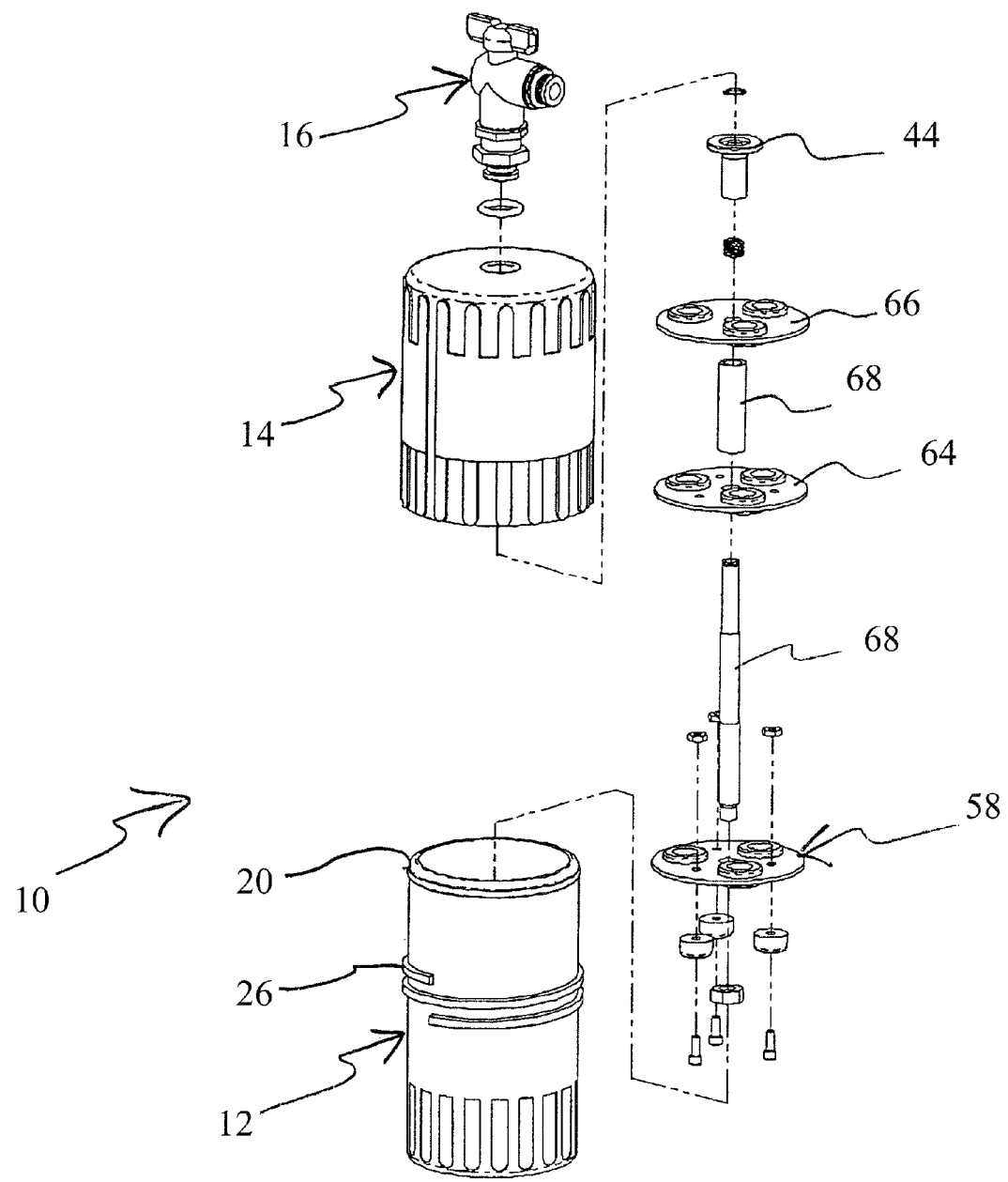
FIG. 7 is an exploded view similar to FIG. 6, illustrating a modified SEM sample holder which uses ⅜ inch sample stubs.

In FIGS. 5-7, there is shown a sample holder 42 for SEM specimens, which comprises a handle 44 having internal threads. SEM samples 48 are disposed on corresponding SEM sample mounts 50 having ⅛ inch pins. Grommet holders 52, hold each SEM sample mount 50. A grommet holder 52 is disposed beneath an additional 1 inch diameter SEM sample mount 54, on a bottom tier platform 58. Set screws 56 are provided for a 1¼ inch metallurgical mount sample. The bottom tier platform 58 is supported on a plurality of support legs 60. Columns 62 function to support platforms 64 and 66, which hold the heretofore described SEM sample mounts 50. The angular distribution of the columns 62 are such that a 1¼ inch diameter sample can be disposed in the center of the bottom tier platform 58. The bottom tier platform 58 can hold either a ⅛ inch pin post sample in the grommet holder 52, or a 1¼ inch diameter metallurgical sample if the grommet 52 is removed and the set screws 56 used instead. The threaded handle 44 is disposed atop and connected to the column 62, which is also threaded. The columns hold the two tiers 64 and 66 in place with fastening hardware (not shown).

FIG. 6 shows an exploded view of the sample holder insert 42 for SEM samples that are mounted on sample mounts with a ⅛ inch diameter column 62. As noted above, the bottom tier holder can hold either a 1 inch diameter SEM sample mount with a ⅛ inch diameter pin, or a 1¼ inch diameter metallurgical mounted sample.

FIG. 7 illustrates a somewhat modified embodiment for holding SEM samples, wherein the sample holder is mounted using ⅜ inch sample stubs.

If a gaseous supply of an inert gas, such as from a nitrogen or argon cylinder, or boil-off from a self-pressurized liquid nitrogen storage tank, is unavailable, then either of two methods discussed below with respect to FIGS. 8 and 9 for generating a suitable clean, dry inert gas may be used.

Figure 8:
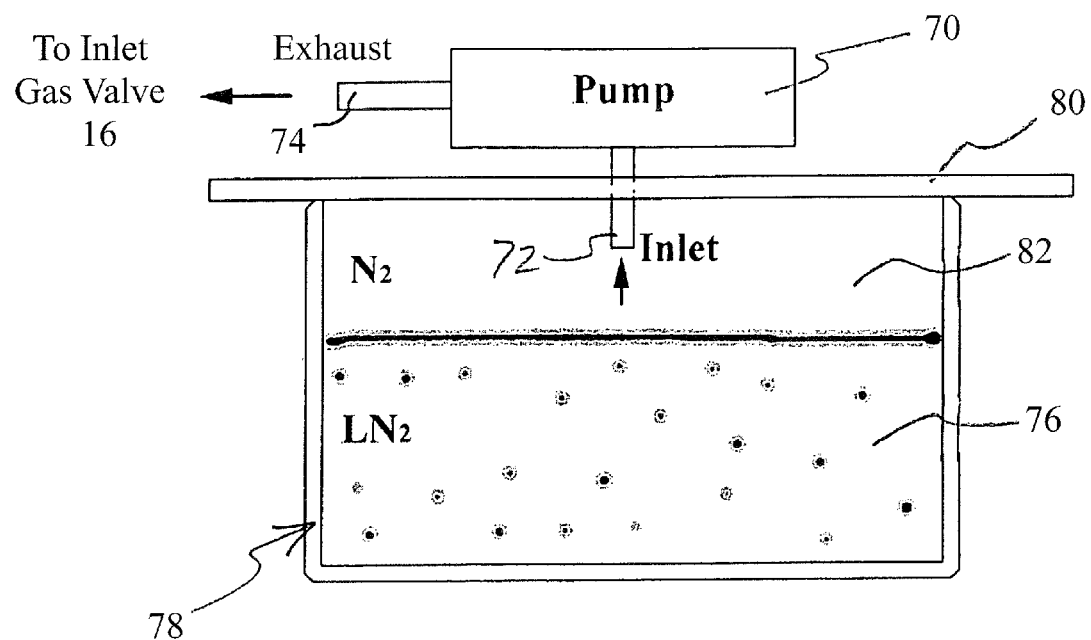
FIG. 8 is a schematic view showing a first method for obtaining gaseous nitrogen for use in the present inventive system.

In FIG. 8, there is shown a schematic diagram for a diaphragm pump supply system used in preferred embodiments of the present invention. As illustrated, a pump 70, preferably a diaphragm pump, has an inlet 72 and an outlet 74. Liquid nitrogen 76 is disposed within an insulated container 78. A top plate 80 covers the container 78, and is sealed. The pump inlet 72 extends through the top sealing plate 80, which also supports the pump 70, and forms a gas tight seal with the sealing plate 80. Gaseous nitrogen from head space 82 in the container 78 enters the pump inlet 72, as shown in the figure. The pump 70 delivers the gaseous nitrogen from the outlet 74 through a flexible tube (not shown) to the inventive system of FIGS. 1-3. Alternatively, gaseous carbon dioxide, obtained from chunks of solid dry ice, may be utilized instead of the nitrogen.

Figure 9:
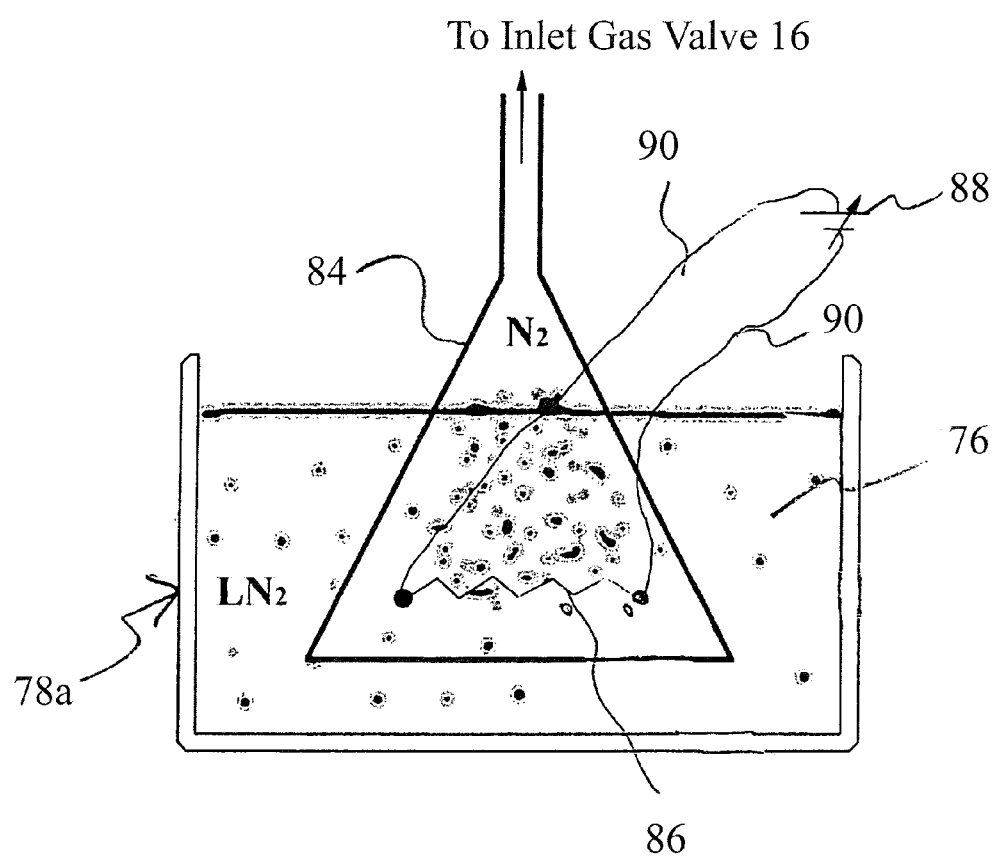
FIG. 9 is a schematic view showing a second method for obtaining gaseous nitrogen for use in the present inventive system.

In FIG. 9, there is shown a schematic diagram for an alternative gaseous nitrogen supply system, which comprises an insulated container 78a having liquid nitrogen 76 therein, as illustrated. An inverted funnel 84 within the container 78a includes a resistive heater 86 which is powered by a variable power supply 88 through electrical leads 90. In this embodiment, the heated resistor functions to boil the liquid nitrogen within the confines of the inverted funnel 84, thereby supplying clean, dry and pure gaseous nitrogen to the inventive system.

Now, with particular reference to FIGS. 1-3, the operation and inventive methods of the present invention will be discussed. As noted previously, the present invention provides a convenient way to preserve a material sample during storage using an inert gas, preferably nitrogen, that replaces the air or other oxygen-containing gas from the volume space of a container.

The container 10 is a two-part container that separates and can be sealed with the presence of an elastomeric O-ring 20 and internal threads 26 on the two portions 12 and 14 of the container. In FIG. 1, after one or more desired material samples are placed on the provided material holder 24, 42, the bottom portion 12 of the container is telescopically received within the top portion 14 of the container sufficiently so that the sealing O-ring 20 is positioned just below the exhaust aperture 22 in the top portion 14. Typically, the operator will insert the bottom portion 12 into the top portion 14 the threads 26 on each container portion 12, 14 first engage. This position is designed to locate the O-ring 20 is in the desired position just below the exhaust aperture 22, as shown in FIG. 1.

As described above, common to all electron microscopy facilities is the availability of liquid nitrogen for cooling X-ray energy dispersive spectrometers, liquid nitrogen vacuum traps, and anti-contamination devices. The boil-off from liquid nitrogen is extremely pure and is relatively easy to produce. Liquid nitrogen is also readily available commercially through local suppliers. In the present inventive method, liquid nitrogen or another suitable inert gas is supplied to the open inlet valve 16 once the O-ring 20 is in the position shown in FIG. 1. This inert gas may be supplied from a commercially available source, or may alternatively be generated by either of the methods shown in FIGS. 8 and 9 and described above, for example. The supplied inert gas flows through the open inlet gas valve 16, into the interior chamber 18, and then out of the chamber 18 through the exhaust aperture 22, thus purging the volume 18 of residual air. The small aperture 22 helps to ensure that the flow of the inert gas helps to drag the original air out of the space 18. The flow may be regulated to be high, initially, in order to help to purge the volume 18 faster and then slowed to a low flow. After a suitable period of time, the inert gas flowing through the container 10 will be at or nearly at its supply purity and not contaminated with remnant gas species from the original atmosphere.

At this point in time, the two container portions 12 and 14 are rotated so that the threaded engagement 26 causes the sealing O-ring 20 to advance upwardly past the small aperture 22, as shown in FIG. 2. In this position, the inert gas flow through the inlet valve 16 stops because it cannot be exhausted from the container. Thus, the assembly of the bottom and top portions 12, 14 of the container 10 together functions similarly to that of an exhaust valve. In FIG. 2, the "exhaust valve" has been closed, and at this time, the inlet valve 16 is also closed, using a stopcock 92 or other suitable means, to prevent further flow into or out of the container 10, thus sealing the inert gas within the interior volume 18. At this point, the pressure within the container 10 is ideally just slightly above atmospheric pressure, because of the relatively low delivery pressure at the end of the purging stage.

Once the valve 16 is closed, the pressure in the container 10 is increased by threading the two portions 12, 14 of the container 10 fully together in relation to one another, such that the volume of the container is decreased. This orientation, wherein the bottom portion 12 has been fully advanced upwardly into the top portion 14, is shown in FIG. 3. The increased pressure in the container 10, created by compressing the volume 18 as the two container halves 12, 14 are fully assembled together, results in two advantages. First, the substantially higher pressure within the container prevents ingress of undesirable reactive gas species into the container. Second, this higher pressure gives positive proof that the samples have been protected during storage and transportation. This latter advantage is evidenced by simply opening the inlet valve 16 while the storage container is compressed, prior to opening it to remove the sample(s) for use. The audible release of gas out of the container when the valve is opened is indicative that the container has not leaked during the storage and/or transport period.

It is possible to use the inventive system without purging in instances when the inventive unit 10 is disposed within a glove box that contains an inert atmosphere. If the container 10 is opened while inside the glove box or glove bag with a suitable inert gas atmosphere, then there is no need to purge the container. As long as the container is sealed while within the glove box, it will be pressurized above the pressure within the glove box by the decrease in volume of the container as it is configured as shown in FIG. 3, after closing the inlet valve 16.

To speed the purging process, the container 10 can be evacuated and then backfilled with inert gas repeatedly as many times as the user desires. To purge in this manner, a three-way valve (not shown) is attached to the inlet valve 16, but externally to the unit 10. This three-way valve is used to switch between the gas supply and a vacuum pump (not shown), which are both attached to the three-way valve. The evacuation takes place, in this method, with the exhaust aperture 22 just closed, so that the container can again be compressed after a final fill of the container with inert gas by threading the container to its FIG. 3 configuration.

Particular advantages of the present invention include, but are not limited to:

1) the clean inert gas introduced into the container ensures that all impurities which may be previously present in the container are fully purged from the container;

2) as noted above, because the container is pressurized, it is easy to determine that no impurities have gained access to the container during the storage period; and 3) it is easy to repeatedly use the inventive container in various laboratory locations, because clean inert gas is typically readily available, or readily capable of being generated using techniques like those taught in this application, at any location utilizing electron microscopes.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A system for preserving material samples, comprising:
   a container having an interior volume, said container comprising a bottom portion having outer walls for defining a portion of the interior volume and a top portion, also having outer walls for defining a portion of the interior volume, wherein the outer walls of said bottom portion are receivable within the outer walls of said top portion in telescoping fashion, and said bottom portion is movable within said top portion to vary the size of said interior volume by varying a height of both the container and the interior volume;
   an inlet opening which is capable of being selectively opened and closed, said inlet opening being adapted for connection to a source of clean inert gas;
   an outlet opening which is capable of being selectively opened and closed, said outlet opening being adapted for exhausting gas from said interior volume; and
   a specimen sample holder, comprising either a SEM specimen holder for holding a SEM specimen or a TEM sample holder for holding a TEM sample, disposed within said interior volume;
   wherein said inlet opening comprises an inlet gas valve.

2. The system as recited in claim 1, wherein said outlet opening is disposed on said container top portion.

3. The system as recited in claim 2, and further comprising a sealing O-ring disposed on an outer surface of said container bottom portion.

4. The system as recited in claim 1, wherein said clean inert gas comprises nitrogen.

5. The system as recited in claim 1, and further comprising threads disposed on each of said top container portion and said bottom container portion for engaging said top container portion with said bottom container portion and permitting relative movement between said top and bottom container portions.

6. The system as recited in claim 1, wherein relative movement between said bottom and top container portions cause said outlet opening to be selectively opened or closed.

7. The system as recited in claim 1, and further comprising a source of inert gas for said system, said inert gas source comprising:
   a container having liquid inert gas therein and a space above said liquid inert gas containing vaporized inert gas;
   a cover over an open end of said container, a pump disposed on said cover and having an inlet extending through said cover and an outlet;
   wherein said pump outlet is fluidly connected with said inlet opening.

8. The system as recited in claim 1, and further comprising a source of inert gas for said system, said inert gas source comprising:
   a container having liquid inert gas therein;
   an inverted funnel disposed in said container, such that a wide mouth of said funnel is disposed within said liquid inert gas, and a narrow spout of said funnel is disposed above said liquid inert gas; and
   a resistive heater disposed within the mouth of said funnel for heating and boiling off gaseous nitrogen from the liquid nitrogen within the funnel;
   wherein the funnel spout is fluidly connected to said inlet opening.

9. A system for preserving material samples, comprising:
   a container having an interior volume, said container comprising a bottom portion having outer walls for defining a portion of the interior volume and a top portion also having outer walls for defining a portion of the interior volume, wherein said top portion and said bottom portion are movable relative to one another to vary a size of said interior volume by varying a height of both the container and the interior volume;
   an inlet opening which is capable of being selectively opened and closed, said inlet opening being adapted for connection to a source of clean inert gas;
   an outlet opening which is capable of being selectively opened and closed, said outlet opening being adapted for exhausting gas from said interior volume; and
   a specimen sample holder disposed within said interior volume;
   said outlet opening being opened or closed by relative movement of said top and bottom container portions, wherein the outlet opening is closed by moving the outer wall of the bottom portion of the container to cover the outlet opening, and the outlet opening is opened by moving the outer wall of the bottom portion of the container to uncover the outlet opening.

* * * * *